United States Patent [19]

Morehouse

[11] Patent Number: 5,354,559
[45] Date of Patent: Oct. 11, 1994

[54] ENCAPSULATION WITH STARCH HYDROLYZATE ACID ESTERS

[75] Inventor: Alpha L. Morehouse, Muscatine, Iowa

[73] Assignee: Grain Processing Corporation, Muscatine, Iowa

[21] Appl. No.: 42,757

[22] Filed: Apr. 6, 1993

Related U.S. Application Data

[63] Continuation of Ser. No. 809,215, Dec. 16, 1991, abandoned, which is a continuation of Ser. No. 529,340, May 29, 1990, abandoned.

[51] Int. Cl.$^5$ ............................ A61K 9/14; A61K 9/26
[52] U.S. Cl. ................................ 424/488; 424/405; 424/410; 424/439; 424/488; 424/493; 424/499; 510/60; 536/110

[56] References Cited

U.S. PATENT DOCUMENTS

| | | | |
|---|---|---|---|
| 2,613,206 | 10/1952 | Caldwell | 260/233.5 |
| 2,661,349 | 12/1953 | Caldwell et al. | 536/63 |
| 3,091,567 | 5/1963 | Wurburg et al. | 424/418 |
| 3,455,838 | 7/1969 | Marotta et al. | 428/402.2 |
| 3,499,962 | 3/1970 | Wurburg et al. | 424/35 |
| 3,663,369 | 5/1972 | Morehouse | 435/99 |
| 3,849,194 | 11/1974 | Armbruster | 435/202 |
| 4,035,235 | 7/1977 | Richards et al. | 195/31 R |
| 4,059,458 | 11/1977 | Germino | 106/213 |
| 4,276,312 | 6/1981 | Merritt | 426/96 |
| 4,812,445 | 3/1989 | Eden et al. | 514/60 |
| 4,977,252 | 12/1990 | Chiu | 536/102 |

*Primary Examiner*—Gollamudi Kishore
*Attorney, Agent, or Firm*—Fitch, Even, Tabin & Flannery

[57] ABSTRACT

Improved encapsulated products comprising a matrix of a starch hydrolyzate acid ester having a water-insoluble material encapsulated therein. In preferred embodiments, a reducing sugar is employed in the encapsulating process and the starch hydrolyzate ester is refined and an acid in combination with an acid salt is used in forming the starch hydrolyzate acid ester.

5 Claims, No Drawings

ENCAPSULATION WITH STARCH HYDROLYZATE ACID ESTERS

This application is a continuation, of application Ser. No. 07/809,215 filed Dec. 16, 1991, now abandoned, which in turn is a continuation of Ser. No. 07/529,340 filed May 29, 1990, now abandoned.

This invention relates to encapsulated products and their manufacture.

Volatile flavoring oils and perfumes are used in a wide variety of applications, such as foods, pharmaceuticals, detergents, insecticides and others. The volatile oils are subject to evaporation and/or oxidation which produces an undesirable flavor or odor. A widely used method of combatting these problems is to encapsulate the volatile oils in a solid matrix which reduces evaporation loss and also provides protection from oxidation.

Starch-acid esters have found use as solid, protective encapsulating agents for oils which can be perfumes, flavors, etc. U.S. Pat. Nos. 2,613,206, 2,661,349, 3,091,567, 3,455,838 and 4,035,235 relate to the preparation of starch-acid esters from granular starch and their use. While such starch-acid esters have found use as encapsulating agents, they exhibit disadvantages, e.g., undesirable color, unpleasant flavor or odor and unsatisfactory shelf life for encapsulated materials which are sensitive to oxygen. The presence of off-flavor or unpleasant odor or off-color is a serious disadvantage, especially when used to encapsulate a delicate characteristic food flavor.

It is therefore a principal object of this invention to provide a new class of encapsulating agents.

It is a further object of this invention to provide for encapsulation of water insoluble oils, flavors, perfumes and the like in a manner to reduce undesirable off-flavor, odor and/or off-color of the encapsulated product.

It is a still further object of this invention to provide oxygen-sensitive encapsulated products having significantly improved stability against oxidation.

It has now been discovered that acid esters of relatively low dextrose equivalent starch hydrolyzates function as effective encapsulating agents and provide improved characteristics with respect to color, flavor, odor and protection of the encapsulated materials against oxidation.

The present invention provides improved encapsulated products comprising a matrix of a starch hydrolyzate acid ester having a water-insoluble material encapsulated within said matrix.

The improved encapsulated products are prepared by forming an aqueous dispersion of a starch hydrolyzate acid ester, adding a water-insoluble substance to be encapsulated thereto, and emulsifying the mixture. The resultant emulsion is then dried to form particles containing the water-insoluble substance encapsulated within the matrix of the starch hydrolyzate acid ester.

The improved encapsulating agents of this invention are produced from starch hydrolyzates (a mixture of glucose polymers) having a dextrose equivalent (D.E.) value of not more than about 30; D.E. value being a measure of the reducing sugar content of the hydrolyzate calculated as dextrose and expressed as a percentage of the total dry substance. Preferably, the starch hydrolyzate is a refined hydrolyzate, i.e., one which has been filtered and treated with carbon, but refining can be conveniently conducted after formation of the starch hydrolyzate acid ester.

The starch hydrolyzate is reacted in aqueous alkaline medium with an anhydride of a substituted dicarboxylic acid to form a starch hydrolyzate acid ester which is then neutralized and dried by a suitable method, preferably by spray drying. The starch hydrolyzate acid esters can be prepared basically by procedures well known in the art, such as, for example, by the methods described in U.S. Pat. Nos. 2,661,349, 3,091,567 and 3,455,838.

In a typical preferred procedure for preparing the starch hydrolyzate acid esters, the starch hydrolyzate is dissolved in water at a concentration of say 20 to 60% solids, usually about 35%, adjusted to a pH of about 8 to 10 with an alkali such as sodium hydroxide and mixed with a substituted dicarboxylic anhydride at a level of from 1 to 5% by weight of the starch hydrolyzate. The reaction proceeds more readily at higher temperatures and it is thus preferred, but not necessary, to conduct the reaction at elevated temperatures of from about 40° to 80° C. During the esterification reaction the pH is preferably maintained in the range of 7 to 9 by the addition of alkali. When the pH is stabilized, indicating the reaction is complete, the reaction mixture is neutralized with a suitable acid, such as hydrochloric acid, sulfuric acid, phosphoric acid, citric acid, malic acid, fumaric and tartaric or an acid salt containing a polyvalent metal ion, such as aluminum sulfate, magnesium sulfate, copper sulfate, ferrous sulfate, stannic chloride, calcium sulfate, barium chloride and the like to achieve a pH in the range of about 3 to 6. When the encapsulated product is intended for food applications, an edible acid such as citric, malic, lactic or phosphoric and the like is preferably employed for neutralization. The reaction mixture is then preferably treated with carbon to absorb protein, color and flavor and filtered. The filtrate is then evaporated and dried by any suitable means, such as spray drying, drum drying, oven drying, etc. to a white powder.

In a preferred embodiment of this invention, the starch hydrolyzate acid ester is neutralized with a combination of an acid salt such as aluminum sulfate and the like and an edible acid such as citric, malic, phosphoric and the like. The addition of 0.1 to 1.0% by weight of the ester of an edible acid such as citric acid enhances the emulsion properties of the starch hydrolyzate acid ester by providing a smaller oil droplet size and producing a more stable emulsion. The reasons for the improved emulsion is not fully understood but may be related to the buffering effect of the acid. Another postulate is that the citric acid acts as a catalyst during the drying step and tends to promote dextrinization of the hydrolyzate acid ester which in turn produces improved emulsion stability and better encapsulation of volatile oils.

The reaction of the substituted dicarboxylic anhydride with the starch hydrolyzate proceeds rapidly, thus the reaction can conveniently be carried out in continuous fashion using a tubular reactor or a series of stirred tank reactors. Since the starch hydrolyzate matrix is a water-soluble compound, the reaction can be run at higher temperatures than possible with granular starch which tends to gelatinize and set up to a solid mass if heated above temperatures of about 55° C. The preferred higher reaction temperatures on the order of 60° to 80° C. provide faster reactions which is a distinct advantage for the continuous process.

The preparation of encapsulated materials employing the products of this invention as the encapsulating matrix can be done by methods well known in the art. Thus, preparation of the encapsulated materials can be accomplished by first preparing a water solution of the starch hydrolyzate acid ester. The concentration of this solution can range between about 10 and 60% solids by weight, more usually between about 40 and 50% solids. The water-insoluble oil or perfume or flavor material to be encapsulated is added with mixing and the dispersion is homogenized to obtain a stable emulsion. This emulsion is then dried by any suitable means, such as spray drying, drum drying, etc. The level of the water-insoluble oil, flavor, perfume or other encapsulate which is blended with the starch hydrolyzate acid ester can range from about 1 to 50% of the solids in the mixture, with a 30% level being typical.

In a particularly preferred but optional embodiment of the invention, a reducing sugar such as glucose, fructose, maltose or lactose and the like is incorporated and mixed with the dispersion of the starch hydrolyzate acid ester and the material to be encapsulated during the encapsulation procedure. The sugar is employed in an amount of 0.5 to 10% by weight of the starch hydrolyzate acid ester. The addition of a reducing sugar in the dispersion of starch hydrolyzate acid ester and the material to be encapsulated appears to enhance the encapsulation process by providing a more stable emulsion of the water insoluble constituent in the aqueous solution of starch hydrolyzate acid ester and increasing the stability (shelf life) of oxygen-sensitive encapsulated constituents after drying. Again, the beneficial effect of reducing sugars on emulsion stability is not fully understood but is evidenced by smaller average oil droplet size in the emulsion which can be seen readily during microscopic examination. The longer shelf life also may be related to the smaller oil droplet size or it may be related to the antioxidant properties of reducing sugars. However, it should be understood that I am not to be bound by my speculation or theories expressed herein as to why benefits are achieved.

The starch hydrolyzates which are employed according to this invention can be derived from corn, waxy maize, tapioca, potato or other waxy or non-waxy starches. The preferred starting materials are partial hydrolyzates derived by converting liquified starch with acid, enzymes, or a combination of acid and enzymes to a dextrose equivalent value (D.E.) between about 10 and about 30.

The starting starch hydrolyzates or the starch hydrolyzate acid esters can be refined by filtration and carbon treatment as known in the art to remove impurities which may contribute to off-color and off-flavor. The preparation and refining of starch hydrolyzates is well known in the art and processes for their preparation are described in the patent literature, such as, for example, U.S. Pat. Nos. 3,663,369, 3,849,194 and others. Partial starch hydrolyzates such as these may be referred to as maltodextrins or corn syrup solids and are commercially available under such trade names as MALTRIN ® (Grain Processing Corporation), STAR-DRI ® (A. E. Staley Company) and LoDex ® (American Maize-Products Company).

Refining of the starch hydrolyzates or esters can be conducted, for example, by adding 0.1 to 2.0% activated carbon to the crude hydrolyzate or ester, dry basis, heating to a temperature of 50°-100° C. with mixing for a period sufficient to adsorb the color and flavor impurities contained therein, adding an inert filter aid and filtering through a fine filter to remove the carbon and other insoluble impurities.

The starch hydrolyzate acid esters are prepared from the anhydride of a substituted dicarboxylic acid having the following formula:

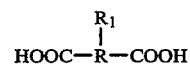

wherein R is a radical selected from the group consisting of dimethylene and trimethylene and $R_1$ is a hydrocarbon substituent selected from alkyl, alkenyl, aralkyl and aralkenyl groups. Preferred substituted dicarboxylic acids falling within this formula are substituted succinic and glutaric acids and their anhydrides, such as decenyl succinic anhydride, octenyl succinic anhydride, dodecenyl succinic anhydride, decenyl glutaric anhydride and the like.

The starch hydrolyzate acid esters of the invention can be represented by the formula:

wherein R and $R_1$ are as identified above. It will be noted that a free carboxyl group is present in the esters which, depending on the pH, may exist in the carboxylate salt form.

The efficiency of the encapsulation process is related to the stability of the emulsion which is obtained when the water-insoluble encapsulate is dispersed in the aqueous solution of the starch hydrolyzate acid esters. The smaller the size of the encapsulate droplets the more stable the emulsion will be, and when the emulsion is dried a higher proportion of the encapsulate will be retained, i.e., encapsulated, in the dried powder. Thus, one way of comparing the encapsulating efficiency of different samples is to observe the relative stability of the emulsion when allowed to stand at room temperature. An unstable emulsion which separates in a few minutes generally will not provide satisfactory encapsulation.

Another method of evaluating encapsulating properties is to examine the emulsion with a microscope and estimate the average size of the insoluble droplets. If the average size of the insoluble droplets is below about 5 microns, the emulsion will remain stable for several weeks and provide satisfactory encapsulation. On the other hand, if the droplet size is larger than about 10 microns, the emulsion will be unstable and the encapsulation efficiency poor.

The following examples illustrate the advantages of the present invention.

EXAMPLE 1

A 50% solution of a 10 D.E. maltodextrin (MALTRIN ® M-100 commercially available from Grain Processing Corporation, Muscatine, Iowa) was prepared using 700 grams of the maltodextrin and 700 grams distilled water. The maltodextrin solution at 32° C. was adjusted to pH 8 with NaOH (1N) and stirred vigorously while adding 14 grams n-octenyl succinic anhydride. Sodium hydroxide was added as needed to maintain the pH at approximately 8. After 1 hour the solution was divided into portions for treatment with aluminum sulfate, citric acid and glucose as shown below. The sample solutions were then freeze dried and the dried powders subjected to dry state heating at 135° C. for 2 hours. The dry roasted starch hydrolyzate-octenyl succinic acid ester samples were used to prepare orange oil emulsions by stirring together 30 grams of the hydrolyzate-acid ester sample, 45 grams water and 7 milliliters orange peel oil.

Evaluation of the samples is shown in Table 1.

TABLE 1

| | Weight % Composition (Dry Basis) | | | | | |
|---|---|---|---|---|---|---|
| Sample | Maltrin M-100/OSA* | $Al_2(SO_4)_3 \cdot 16H_2O$ | Citric Acid | Glucose | Emulsion Stability | Oil Droplet Size |
| 1 | 100 | 1 | 0 | 0 | Good | Approximately 2–8$\mu$ |
| 2 | 95 | 1 | 0 | 4 | Very Good | Approximately 2–4$\mu$ |
| 3 | 94.5 | 1 | 0.5 | 4 | Very Good | Approximately 1–2$\mu$ |
| Maltrin-100 alone (Control) | | | | | Poor | Complete separation in 30 minutes |

*A 10 D.E. starch hydrolyzate octenyl succinic ester

These results show that samples 1, 2 and 3, which were starch hydrolyzate-octenyl succinate esters, produced stable emulsions whereas the maltodextrin (MALTRIN ® M-100) alone did not produce a stable emulsion. The results also show that the oil droplet size was smaller and emulsion stability was improved by the incorporation of the reducing sugar, glucose.

EXAMPLE 2

A slurry of corn starch was partially hydrolyzed by heating with acid followed by treatment with alpha-amylase to provide a hydrolyzate having a D.E. of about 10. The hydrolyzate was refined by filtering and treating with carbon. Two thousand five hundred grams of an aqueous solution of this refined hydrolyzate containing 700 grams of solids were heated to 38° C. and 14.5 grams of n-octenyl succinic anhydride mixed therewith. Sodium hydroxide (1N) was added as needed to maintain the pH at 8.0 (total sodium hydroxide=84 milliliters). After 1 hour the reaction mixture was neutralized with 10.5 grams aluminum sulfate ($Al_2(SO_4)_3 \cdot 16H_2O$) and 3.6 grams citric acid.monohydrate. The solution was warmed to 85° C., heated with 3.5 grams carbon for 10 minutes and filtered to provide a clear solution of hydrolyzate-octenyl succinate ester.

The solution of the hydrolyzate octenyl succinate ester was divided into four equal portions, treated with 0, 2, 4 and 6 weight percent glucose, dry basis, and freeze dried. The dried samples were placed in a rotary reactor and heated in the dry state, under vacuum, for 1 hour at 135° C. The emulsion stabilizing properties of the dry roasted samples were compared by forming emulsions with orange oil (30 grams of ester, 40 grams water plus 7 milliliters orange oil). Evaluation of these samples are summarized in the following table:

lyzates and show that the addition of glucose to the reaction mixture prior to drying enhances the stability of emulsions prepared with the ester.

EXAMPLE 3

This example describes the preparation of the octenyl succinate ester of 20 D.E. corn syrup solids.

Two thousand nine hundred grams of corn syrup solids having a D.E. of about 20 (MALTRIN ® M-200 available from Grain Processing Corporation, Muscatine, Iowa) were dissolved in 7,200 milliliters water and adjusted to pH 8 with sodium hydroxide. The solution was heated to 40° C. and 56 grams n-octenyl succinic anhydride were added. The mixture was stirred vigorously and the pH maintained at 8 by continuous addition of one normal sodium hydroxide. When the pH became constant (approximately 30 minutes), 42 grams aluminum sulfate and 15 grams citric acid were added. The solution was decolorized by treating with carbon at 90° C. for 10 minutes followed by filtration. Fifty-two grams glucose were added and the product recovered by freeze drying.

EXAMPLE 4

The procedure described in Example 3 was repeated using a 10 D.E. maltodextrin (MALTRIN ® M-100) in place of the 20 D.E. corn syrup.

EXAMPLE 5

The freeze dried samples from Examples 3 and 4 were placed in a rotary reactor and heated in the dry state under vacuum for 1 hour at 135° C. Both samples were compared for flavor oil encapsulation properties with a leading commercial encapsulating agent which is an octenyl succinate ester of granular starch.

The procedure for the encapsulation comparison was as follows:

The samples were dissolved in warm water to provide a 50% solids solution. Orange peel oil was added at a level of 20% of the total solids, the mixture homogenized to form an emulsion and the emulsion spray dried. The dried powder was analyzed for oil recovery, extractable oil, mean particle size and shelf life

TABLE 2

| Sample | Aluminum Sulfate % | Citric Acid % | Glucose % | Relative Emulsion Stability 3 Days, Room Temperature | Oil Droplet Size $\mu$ |
|---|---|---|---|---|---|
| 5 | 1.5 | 0.5 | 0 | Fair, moderate oil separation | 2–20 |
| 6 | " | " | 2 | Good, very slight oil separation | 1–5 |
| 7 | " | " | 4 | Very good, very slight oil separation | 1–2 |
| 8 | " | " | 6 | Very good, very slight oil separation | 1–2 |

The above results demonstrate the preparation of octenyl succinate esters of the low D.E. starch hydro- (number of days for limonene oxide to form). The results are summarized below:

TABLE 3

| Sample | Type | Emulsion Properties | Extractable Oil mg/100 g | Total, Oil g/100 g | Particle Size Average micrometers* | Shelf Life Days |
|---|---|---|---|---|---|---|
| 9 | M-200 starch hydrolyzate octenyl succinate ester | Good, slight oil separation | 3.9 | 18.1 | 0.70 | 45 |
| 10 | M-100 starch hydrolyzate octenyl succinate ester | Very good, no oil separation | 11.3 | 17.7 | 0.62 | 28 |
| 11 | Commercial starch ester encapsulant | Very good, no oil separation | 149 | 16.0 | 0.64 | 12 |

*Microtrac particle size analysis.

The results in the table above show that the octenyl succinate esters of the 10 and 20 D.E. starch hydrolyzates provided emulsion stability, as measured by particle size, comparable to the leading commercial encapsulant. However, with the starch hydrolyzates the total amount of encapsulated orange oil was higher and the shelf life was much better. This difference in shelf life is significant and constitutes an important advantage of the present invention.

EXAMPLE 6

This experiment illustrates the improvement in emulsion stabilization which is provided when glucose is added to the octenyl succinate ester of low D.E. starch hydrolyzate.

An octenyl succinate ester of a 10 D.E. maltodextrin was prepared using 1,450 grams MALTRIN ® M-100, 3,000 grams water and 28 grams octenyl succinic anhydride. The maltodextrin and anhydride were reacted at 50° C. and at a pH of 9. The ester was neutralized with 21 grams aluminum sulfate and 7.5 grams citric acid.-monohydrate. After carbon treatment and filtration, the product was treated with 0, 2 and 4 weight percent glucose, dry basis. Portions of the dried samples were dry roasted 1 hour at 135° C. and compared for emulsion stabilizing capacity. The results are shown below:

compared to prior art esters made with granular starch. It also shows the improvement in shelf life obtained from addition of a reducing sugar.

Samples of 10 and 20 D.E. maltodextrins (MALTRIN ® M-100 and MALTRIN ®M-200, respectively, available from Grain Processing Corporation, Muscatine, Iowa) were esterified with 2 weight percent n-octenyl succinic anhydride using the procedures described in Example 3. The reaction mixture was neutralized with 1.5 weight percent aluminum sulfate and 0.5 weight percent citric acid (dry basis), decolorized with carbon and filtered. Both samples were subdivided into three parts, mixed with 0, 2.5 and 5 weight percent glucose and spray dried.

The encapsulation test was run using orange peel oil to make an emulsion which was spray dried. The dried powder was analyzed to determine total oil retention, extractable oil, particle size and shelf life.

The results of the test are summarized in the table below. The data show that total oil retention in the products of the invention is as good as in a leading commercial starch based encapsulating agent. There is a marked difference in shelf life with the products of the present invention, which exhibit much longer shelf life than the commercial encapsulant. In the M-100 series there is also an improvement from the added glucose in the form of a 50% increase in shelf life.

TABLE 4

| Sample | | % Glucose | Particle Size, μ (3 days) | Emulsion Properties (After 5 Weeks Storage) |
|---|---|---|---|---|
| 12 | Starch hydrolyzate ester | 0 | 2–15 | Good, no separation |
| 13 | Starch hydrolyzate ester | 2 | 1–3 | Very good, no separation of oil |
| 14 | Starch hydrolyzate ester | 4 | 1–3 | Very good, no separation of oil |
| 15 | Starch hydrolyzate alone (Control) | — | 10–50 | Poor, complete separation of oil |

EXAMPLE 7

This example further illustrates the superior encapsulating properties of acid esters of starch hydrolyzates

TABLE 5

| Sample No. | Type | % Glucose | Total Oil g/100 | Extractable Oil mg/100 | Particle Size Micrometers* | Shelf Life Days |
|---|---|---|---|---|---|---|
| 17 | M-200 Starch Hydrolyzate | 0 | 19.10 | 1.67 | 1.86 | 21 |
| 18 | M-200 Starch Hydrolyzate | 2.5 | 19.96 | 2.56 | 1.67 | 21 |
| 19 | M-200 Starch Hydrolyzate | 5.0 | 19.79 | 2.63 | 1.75 | 21 |
| 20 | M-100 Starch Hydrolyzate | 0 | 19.62 | 13.14 | 1.79 | 4 |
| 21 | M-100 Starch Hydrolyzate | 2.5 | 19.20 | 2.38 | 1.74 | 5 |

TABLE 5-continued

| Sample No. | Type | % Glucose | Total Oil g/100 | Extractable Oil mg/100 | Particle Size Micrometers* | Shelf Life Days |
|---|---|---|---|---|---|---|
| 22 | M-100 Starch Hydrolyzate | 5.0 | 19.62 | 1.82 | 1.66 | 6 |
|  | Commercial Encapsulant | — | 20.8 | 1.89 | 1.85 | 2 |

*Microtrac particle size analysis.

The starch hydrolyzate acid esters of this invention can be used as the encapsulating matrix for a variety of water-insoluble materials, such as encapsulated products used as perfumes, pharmaceuticals, detergents, insecticides and so forth. The new encapsulating agents are particularly useful to encapsulate materials which are volatile or sensitive to oxidation. Food flavors such as orange oil, lemon oil or other fruit flavors can be encapsulated in a stable, powder form which will provide for controlled release of the flavor at a later time.

Since the preferred encapsulating agents of this invention are refined, they are virtually free of any color or off-flavor which might alter or diminish the odor, flavor and appearance of the encapsulated material. This is a distinct advantage over the dextrinized starch acid-esters of the prior art which have a characteristic odor and flavor which mask the flavor and odor of the encapsulate. Also, the starch hydrolyzate acid esters of this invention provide a significant advantage over granular starch acid esters of the prior art with respect to protection of oxygen-sensitive encapsulates. Long shelf life of various encapsulated materials is an important desideratum.

Those modifications and equivalents which fall within the spirit of the invention are to be considered a part thereof.

What is claimed is:

1. A composition comprising a particulate matrix of a starch hydrolyzate acid ester having encapsulated therein a water insoluble material selected from the group consisting of food flavors, perfumes, pharmaceuticals and insecticides, said hydrolyzate acid ester being the reaction product of a substituted succinic or glutaric acid or the anhydrides thereof with a starch hydrolyzate which is refined by carbon treatment and having a dextrose equivalent of about 10 to 30 which is substantially free of granular starch, the substituted succinic or glutaric acid having the formula:

$$\overset{R_1}{\underset{|}{HOOC-R-COOH}}$$

wherein R is a radical selected from the group consisting of dimethylene and trimethylene and $R_1$ is a hydrocarbon substituent selected from alkyl, alkenyl, aralkyl and aralkenyl.

2. A composition in accordance with claim 1 wherein said particulate matrix includes a reducing sugar in an amount from about 0.5 to 10% by weight of the starch hydrolyzate acid ester.

3. A composition in accordance with claim 1 wherein the reducing sugar is glucose.

4. A composition in accordance with claim 1 wherein the said starch hydrolyzate is refined by treatment with carbon and filtered.

5. A composition in accordance with claim 4 wherein the starch hydrolyzate acid ester is an ester of octenyl succinic acid.

* * * * *